US005705338A

United States Patent [19]

Piran et al.

[11] Patent Number: 5,705,338
[45] Date of Patent: Jan. 6, 1998

[54] REDUCTION OF BACKGROUND IN NONCOMPETITIVE BINDING ASSAYS

[75] Inventors: Uri Piran; Laurie Ann Livshin, both of Sharon; Richard A. Martinelli, Brighton; William J. Riordan, Mansfield; John T. Unger, Medfield, all of Mass.

[73] Assignee: Chiron Diagnostics Corporation, Walpole, Mass.

[21] Appl. No.: 434,743

[22] Filed: May 4, 1995

Related U.S. Application Data

[63] Continuation-in-part of Ser. No. 121,806, Sep. 15, 1993, Pat. No. 5,445,936.

[51] Int. Cl.$^6$ .............................. C12Q 1/68; G01N 33/53; G01N 33/547; G01N 33/543
[52] U.S. Cl. ........................ 435/6; 435/7.5; 435/7.94; 436/518
[58] Field of Search .................... 435/6, 7.5, 7.8, 435/7.92, 7.94, 962; 436/500, 518, 526, 527, 532, 538, 541, 513

[56] References Cited

U.S. PATENT DOCUMENTS

| | | | |
|---|---|---|---|
| 3,654,090 | 4/1972 | Schuurs | 435/7.93 |
| 4,434,236 | 2/1984 | Freytag | 436/512 |
| 4,551,426 | 11/1985 | Freytag et al. | 435/7.92 |
| 4,670,383 | 6/1987 | Baier et al. | 435/7.92 |
| 4,788,136 | 11/1988 | Grenier et al. | 435/7.92 |
| 5,236,849 | 8/1993 | Ishikawa | 436/540 |
| 5,312,730 | 5/1994 | Piran et al. | 435/7.92 |
| 5,445,936 | 8/1995 | Piran et al. | 435/6 |
| 5,451,504 | 9/1995 | Fitzpatrick et al. | 435/7.2 |

OTHER PUBLICATIONS

Freytag, J.W. et al, 30:3, Clin. Chem. 417–420 (1984).
Hechemy, K.E. et al, Laboratory Management, 27 (Jun. 1984).
Jackson, T.M. et al, 87 J. Immuno Methods, 13–20 (1986).
Law, S.J., et al, 4, J. of Bioluminescence and Chemiluminescence, 88–98 (1989).
Leflar, C.C. et al, 30:11 Clin. Chem., 1809 (1984).
Miles, L.E.M. et al, 219 Nature, 186–189 (1968).
Piran, U. et al., 33/9 Clin. Chem. 1517–1520 (1987).
Piran, U. et al, 39/5 Clin. Chem. 879–883 (1993).
Weetall, H. 166 Science, 615–617, (1969).
Weetall, H., et al., 185 Biochem. Biophys. Acta, 464–465 (1969).

*Primary Examiner*—Marian C. Knode
*Assistant Examiner*—Donna C. Wortman
*Attorney, Agent, or Firm*—Arthur S. Morgenstern; Robert P. Blackburn

[57] ABSTRACT

Novel non-competitive assay techniques have been developed which not only improve sensitivity, but also are convenient and less susceptible to interfering factors. They are compatible with existing instruments and can be run in one or more test tubes. The analyte is reacted with labeled specific binder, after which the mixture is reacted with (1) an insoluble material attached to an analyte derivative and (2) a solid phase carrying a binder. The solid phase is then separated, and the label attached to the solid phase is measured. Variations of the procedure include the use of a reversible bridge for attaching the insoluble material to the analyte mimic and the conduct of the assay in various porous media, such as paper, chromatographic and electrophoretic media, and dipsticks.

7 Claims, 8 Drawing Sheets

ZONE OF CAPTURING ANTI-ANALYTE OR ANTI-LABEL

ZONE OF ARRIVAL OF ANALYTE-LABELED ANTIBODY

ZONE OF IMMOBILIZED ANALYTE MIMIC

DIRECTION OF BUFFER MIGRATION

ZONE OF LABELED ANTIBODY AND ANALYTE DEPOSIT

BUFFER

FIG.7b

BUFFER

FIG.8

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
        ( A ) LENGTH: 47 bases
        ( B ) TYPE: Nucleic acid
        ( C ) STRANDEDNESS: Single
        ( D ) TOPOLOGY: Linear     ( i i ) MOLECULE TYPE: Genomic DNA
        ( A ) DESCRIPTION: DF-508, a portion of the sequence of exon 10 of the CFTR gene surrounding base number 1652 with bases 1653- 1655 deleted.

( x i ) SEQUENCE DESCRIPTION: SEQ ID NO: 1:

GGC ACC ATT AAA GAA AAT ATC ATT GGT GTT TCC TAT GAT    39

GAA TAT AG    47

( 2 ) INFORMATION FOR SEQ ID NO: 2:

( i ) SEQUENCE CHARACTERISTICS:
        ( A ) LENGTH: 24 bases
        ( B ) TYPE: Nucleic acid
        ( C ) STRANDEDNESS: Single
        ( D ) TOPOLOGY: Linear     ( i i ) MOLECULE TYPE: Genomic DNA
        ( A ) DESCRIPTION: 508.CF, bases 1629- 1652 of exon 10 of the CFTR gene     ( x i ) SEQUENCE DESCRIPTION: SEQ ID NO: 2:

AT GAT ATT TTC TTT AAT GGT GCC A    24

( 2 ) INFORMATION FOR SEQ ID NO: 3:

( i ) SEQUENCE CHARACTERISTICS:
        ( A ) LENGTH: 53 bases
        ( B ) TYPE: Nucleic acid
        ( C ) STRANDEDNESS: Single
        ( D ) TOPOLOGY: Linear     ( i i ) MOLECULE TYPE: Other DNA/Genomic DNA
        ( A ) DESCRIPTION: PMP.508, bases 1 - 29 are a spacer of synthetic DNA; bases 30-53 consists of bases 1656-1678 of exon 10 of the CFTR gene     ( x i ) SEQUENCE DESCRIPTION: SEQ ID NO: 3:

CCTAGTCCAA GTACGGCGCC GAAGAGGCC CT ATA TTC ATC ATA GGA    46

AAC ACC A    53

( 2 ) INFORMATION FOR SEQ ID NO: 4:

( i ) SEQUENCE CHARACTERISTICS:
        ( A ) LENGTH: 54 bases
        ( B ) TYPE: Nucleic acid
        ( C ) STRANDEDNESS: Single
        ( D ) TOPOLOGY: Linear     ( i i ) MOLECULE TYPE: Other DNA/Genomic DNA
        ( A ) DESCRIPTION: LCF4, bases 1- 24 consist of bases
            1652-1629 of exon 10 of the CFTR gene; bases
            25-54 consist of a spacer of synthetic DNA     ( x i ) SEQUENCE DESCRIPTION: SEQ ID NO: 4:

T GGC ACC ATT AAA GAA AAT ATC AT GGAGGAGGAG GAGGAGGAGG 44

AGGAGGAGGA 54

( 2 ) INFORMATION FOR SEQ ID NO: 5:

( i ) SEQUENCE CHARACTERISTICS:
        ( A ) LENGTH: 52 bases
        ( B ) TYPE: Nucleic acid
        ( C ) STRANDEDNESS: Single
        ( D ) TOPOLOGY: Linear     ( i i ) MOLECULE TYPE: Genomic DNA/Other DNA
        ( A ) DESCRIPTION: 508.CF-2AE, bases 1 - 24 consist of bases
            1629-1652 of exon 10 of the CFTR gene, bases 25 -52
            consist of a tail of synthetic DNA. The cytidines at
            bases 29 and 43 were synthsized with modified bases
            containing an aliphatic amine.

( x i ) SEQUENCE DESCRIPTION: SEQ ID NO: 5:

AT GAT ATT TTC TTT AAT GGT GCC A CCTACTGCAA CCTACCTACT 44

GCAACCTA 52

REDUCTION OF BACKGROUND IN NONCOMPETITIVE BINDING ASSAYS

This application is a continuation-in-part of application Ser. No. 08/121,806, now U.S. Pat. No. 5,445,936, filed Sep. 15, 1993.

BACKGROUND

In developing a binding assay, it is important that the scientist develop one that has a high level of sensitivity and specificity, can eliminate interfering substances, and is convenient. The discussion herein may emphasize the immunochemical-type assay, but it should be recognized that the descriptions are also applicable to gene probe and other types of binding assays.

Sensitivity

Sensitivity means the minimal detectable dose, namely the smallest mass of analyte that generates a statistically significant change in the signal generated by the assay vs. that obtained in the absence of analyte. There is a need to increase sensitivity of binding assays (i.e., detect smaller amounts of analyte), because in many situations the analytes, whether they are hormones, drugs, microorganisms, toxins, pollutants or genetic materials, exert their effects at low concentrations. Furthermore, high sensitivity allows the use of small sample size, which can help to reduce "sample matrix" interferences. In addition, higher sensitivity allows measuring low analyte concentrations with a higher precision. In discussing sensitivity, immunochemists have often distinguished between competitive assays and non-competitive assays. In a competitive assay, the signal which is measured is that emanating from the specific binder that does not bind analyte. For example, in some competitive assays, the labeled antibody is incubated with a sample containing analyte and a solid phase-immobilized analyte derivative. The labeled antibody that did not bind analyte binds the solid phase, and the signal emanating from the solid phase-bound labeled antibody is measured. In other types of competitive assays, unlabeled antibody is incubated with a sample containing an analyte and a labeled analyte derivative (or analyte mimic). The labeled analyte derivative binds those antibody binding sites that did not bind analyte. By measuring the signal coming from the labeled analyte derivative that bound the antibody, the assayist actually obtains an estimate of the concentration of antibody sites that did not bind analyte. Thus, in both types of competitive assays, one measures signal associated with the fraction of specific binder sites that did not bind analyte. The signal generated from a competitive assay decreases as the analyte concentration increases. Since small levels of analyte correspond to large signals, small changes in low concentrations of analyte lead to small differences between large numbers, which are hard to measure accurately.

A second type of binding assay is the non-competitive type. In this assay, a labeled specific binder, for example a labeled antibody, is incubated with the sample and binds a portion of the analyte. In one variation (type A) of noncompetitive assay, a solid-phase immobilized unlabeled specific binder is added, simultaneously or in sequence, to bind another epitope on the analyte, in which case it is called a "sandwich" assay. For example, the immobilized molecule might be an antibody against a second epitope on the analyte, and the analyte might form a ternary complex with the labeled antibody and an immobilized unlabeled antibody. The solid phase is then washed and the signal measured is the signal that comes from the ternary complex containing the analyte. In this case the signal increases with increasing analyte concentration.

Another variation of the noncompetitive immunoassay (type B) was invented by L. E. M. Miles and C. N. Hales, Nature 219:186, 1968. In this type of assay the labeled antibody is first incubated with the analyte to form an immune complex, and then the mixture is contacted with a solid phase. This solid phase has an analyte derivative (or mimic) in large excess, which causes the unreacted labeled antibody to bind to it. The solid phase is then separated from the liquid phase and a portion of the liquid phase is taken for signal measurement. The difference from the competitive type of assay is that one does not measure the signal associated with the solid phase, namely the labeled binder that did not bind analyte. What one measures, instead, is the signal associated with the labeled binder that bound analyte and consequently did not bind the immobilized binder, thus remaining in the liquid phase.

Type A of the non-competitive assay has the potential for the highest sensitivity. Jackson and Ekins (T. M. Jackson and Ekins, R. P., Journal of Immunological Methods, 87:13, 1986) showed by mathematical analysis that when the specific activity of the label is not limiting, the sensitivity of type A is higher than that of the competitive assay. Empirical data supports the conclusion that type A of immunoassays is more sensitive than the competitive type of immunoassays: several immunoassays, such as thyroid stimulating hormone, have sensitivity of several million molecules per assay cuvette; in contrast, the most sensitive competitive immunoassays, such as those of digoxin and triiodothyronine, have sensitivities of several billion molecules per assay cuvette. Although type A assays are the most sensitive type, there is a need to improve their sensitivities even further, and one way of achieving this improvement is via reduction of "nonspecific binding" (NSB), namely, the nonspecific adsorption of the labeled specific binder to the solid phase and the reaction vessel.

The large gap in potential sensitivity (a number of orders of magnitudes, depending on the value for fractional non-specific binding) between the competitive type and type A of the non-competitive is the main reason for the wide use of type A. The former is used either when high sensitivity is not required or when type A is not possible due to the existence of only one epitope on the analyte, as is the case for analytes that are haptens or short peptides.

Theoretical considerations, first advanced by Miles and Hales, strongly suggest that the type B non-competitive assay, suitable for analytes with one epitope, should also allow higher sensitivity than the competitive type. This is because the formula for calculating sensitivity of type A (see Jackson and Ekins, 1986) can be applied if we replace "Fractional non-specific binding" with its equivalent "Fractional non-specific retention". This latter term is simply the fraction of the unreacted labeled binder that failed to separate from the labeled binder-analyte complex in the liquid phase, much the same as the non-specific binding refers to the unreacted labeled binder that failed to separate from the complex on the solid phase. Thus, from a mathematical standpoint, the non-competitive assay should be more sensitive. The signal increases as the concentration of analyte increases, and low concentrations of analyte can be detected more easily since small differences between small numbers are relatively easy to distinguish, and the signal due to the presence of analyte is distinguished from a small, rather than a large background.

Baier et al. described a non-competitive immunoassay format of type B with an added separation step. After incubating the sample containing analyte with the labeled antibody, a solid phase with immobilized analyte derivative is added to bind the unreacted labeled antibody. The solid phase is separated and an aliquot of the remaining liquid phase is pipetted off to a new reaction cuvette containing a second solid phase. The second solid phase has an immobilized antibody against the labeled antibody or some part of the labeled antibody-analyte complex. The signal associated with the complex captured on the second solid phase is measured. The intent of this additional step was to allow a wash step in order to remove sample matrix interfering factors.

Copending application Serial No. 08/121,806 teaches a method for conducting type B assay with use of two solid phases (the first solid phase was named insoluble material, and the second solid phase was named solid phase) and eliminates the interferences discussed by Baier et al., but utilizes only one container. This simplifies the assay and allows performing the assay with currently existing instruments. However, there is a need to further reduce background and NSB in order to further increase sensitivity in both type A and B noncompetitive assays.

Elimination of Interfering Substances

Often the sample to be analyzed in an immunoassay is delivered in an environment that includes interfering substances. For example, a serum sample not only contains the analyte of interest, but also many components that could interfere with the immunoassay. Immunochemical assay techniques include steps that easily isolate the analyte from the interfering substances. For example, the analyte can be reacted with an antibody which is connected to a solid phase. The solid phase can then be separated from the other components in its environment and analyzed.

The separation step referred to above can be accomplished in one of many ways. For example: an assayist can use non-magnetic particles as the solid phase using either centrifugation filtration as the method of separation, or magnetic particles as the solid phase, in which case the separation is accomplished by the application of a magnetic field. Other effective means of separation involve various chromatographies, electrophoreses, and the use of extended surfaces, such as microtiter plates, large beads, fibers and others. The separation step can be done manually or by an automated or non-automated instrument; in either case, however, the solid phase is separated and washed, the liquid phases are discarded, and the solid phase-associated signal is the one being measured.

Many substances interfere with the assays despite the wash steps. For example, cross-reactants share structural similarities with the analyte and also bind the labeled or unlabeled specific binder. When a cross-reactant binds the labeled specific binder the assay result is falsely elevated. When sufficiently high concentration of a cross-reactant binds the unlabeled specific binder and saturates it, a falsely low result is obtained. Occasionally the analyte itself is present in an extremely high concentration and thereby saturates the unlabeled specific binder, leading to a "high dose hook effect".

Heterophilic antibodies and rheumatoid factors bind antibodies and can either form a bridge between the labeled and unlabeled antibodies or inhibit their desired binding activity, leading to false results.

Convenience

Whether it is done manually or by an automated instrument, the separation step is one of the most technically demanding operations in the assay. It needs to be done rapidly, so that the analyte-binder complex of interest does not dissociate. It also needs to be efficient, so that the unbound labeled binder and interfering substances are nearly completely removed. In addition, it needs to be reproducible, in order to maintain overall high assay precision. These demands on the separation step are the impetus for the development of the various "homogeneous", or "no-separation" assays, where there is no separation of the solid phase. It is clear from this discussion that performing the assay in one container or with use of a dipstick, sensor, or a pseudohomogenous assay, is preferred over the use of two containers with regard to convenience. Another convenient format is the use of porous material, such as chromatographic paper, nitrocellulose paper, electrophoretic gel and similar media in which there is a continuous water phase associated with the porous solid material, such that some binders may be restricted or immobilized to zones via the porous material, and the transport of liquid phase molecules (or complexes) from one zone to another occurs through the continuous liquid phase.

SUMMARY OF THE INVENTION

Novel non-competitive binding assay techniques have been developed which not only improve sensitivity, but also are convenient and less susceptible to interfering factors. They are either compatible with existing instruments and are assays that can be run in one test tube or are convenient due to their dipstick, chromatographic or sensor configurations, or are higher sensitivity assays that require 2 or more separations.

SUMMARY OF THE DRAWINGS

FIG. 7 depicts an assay format utilizing a chromatographic paper as a porous material. In this format the sample reacts with the labeled specific binder in one zone, then an aqueous medium causes the migration of the reacted and unreacted labeled specific binder to a zone containing an immobilized analyte mimic immobilized, and the reacted labeled specific binder continues to migrate away from that zone. A second aqueous medium then causes migration of the reacted labeled specific binder in a different direction toward a zone with an immobilized second specific binder, which captures the analyte-labeled specific binder complex, followed by readout of the label. If the analyte mimic is immobilized via a reversible bridge, a solution containing a material that disrupts the bridge can be migrated in any of the directions shown as an arrow with a broken line in order to further reduce background signal, followed by readout of the label. Finally, a detergent solution washes the complex to reduce the NSB caused by traces of migrating unreacted labeled specific binder-analyte mimic-liposome.

DETAILED DESCRIPTION OF THE INVENTION

Convenient binding assay techniques that have improved sensitivity and are less susceptible to interfering substances are described herein. One of its primary applications is in the field of immunochemistry, and, thus, most of the discussion of the techniques is related to the immunochemistry field. However, it should be noted that the techniques are equally applicable to other binding assays, such as gene probe assays and receptor assays. These assay techniques are suitable for a wide diversity of analytes, including those with one or more epitopes. Analytes may include proteins, peptides, drugs, hormones, environmental pollutants, nucleic acids, lipids, carbohydrates and various conjugates of these. The technique is suitable for both determination of the total amount of analyte in the sample or the free fraction (e.g. free hormones and free drugs in biological fluids).

Figure 1:
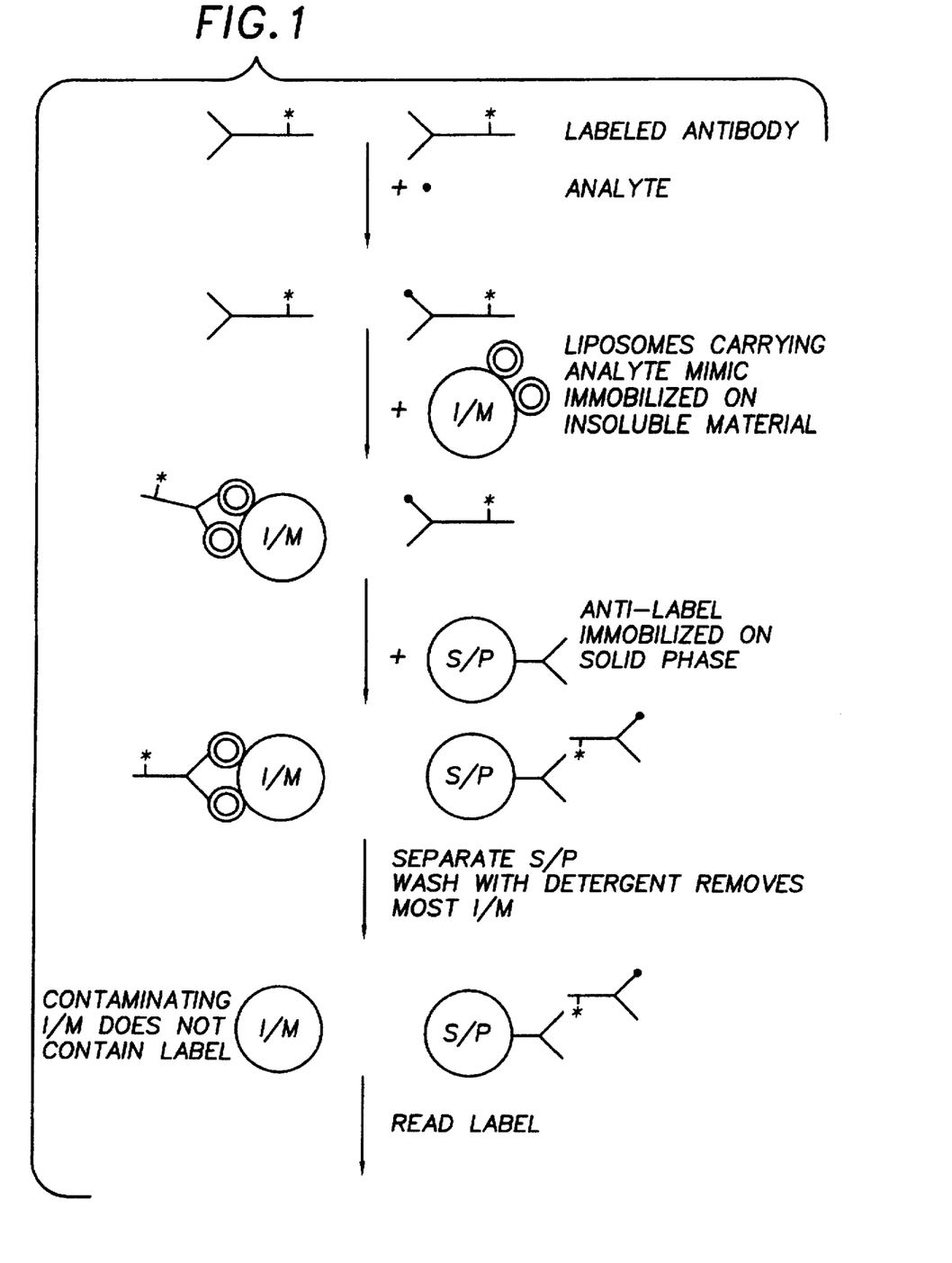
FIG. 1 shows the format of an assay for a monoepitopic analyte when the analyte mimic is attached to the insoluble material via a reversible bridge, the reversible bridge being a liposome, and the assay is conducted in one container.

One aspect of the instant invention is an improvement on the invention of type B noncompetitive assay performed in one cuvette, as described in Ser. No. 08/121,806. The inventors found that small amounts (0.01%–1%) of the insoluble material-labeled specific binder remain in the cuvette together with the solid phase after the wash steps, and since this residual insoluble material is complexed with labeled specific binder, it contributes to background signal. Because the amounts of insoluble material which remains associated with the solid phase is relatively small, it is called herein contaminating insoluble material. Although the amounts of contaminating insoluble material is relatively small it is desirable to remove it in order to reduce the background signal. Therefore, the present invention utilizes a reversible bridge between the insoluble material and the analyte mimic immobilized upon it, in conjunction with a wash solution that dissociates (or disrupts) the analyte mimic-labeled specific binder complex from the insoluble material during the wash step. Reversible bridge is a means of coupling two or more molecules, macromolecules or particles to each other such that the bond between these components is stable enough during manufacture, storage and use in the assay up to the point in time when it is desirable to disrupt it. The disruption leads to separation of the components; therefore, reversible bridges are devices for bonding the components temporarily. Such reversible bridges were used as part of the process of "immune complex transfers"; see Ishikawa et al. Clinica Chimica Acta (1989) 185:223 and Piran et al. (1994) U.S. Pat. No. 5,312,730 for descriptions of various reversible bridges and methods for their preparation. A reversible bridge can be a chemical covalent bond or preferably a noncovalent bond such as an immunochemical bond, such as anti-DNP/DNP, or a lipophilic bridge, such as a liposome or any of the bridges described in the above publications by Ishikawa et al. and Piran et al. The reversible bridge keeps the components bonded until a material that is capable of disrupting the reversible bridge is added. For example, if the reversible bridge is a lipophilic material, such as a liposome, the material capable of disrupting the reversible bridge is a solution of detergent or surfactant or a lipolytic enzyme. (See FIG. 1)

Figure 2:
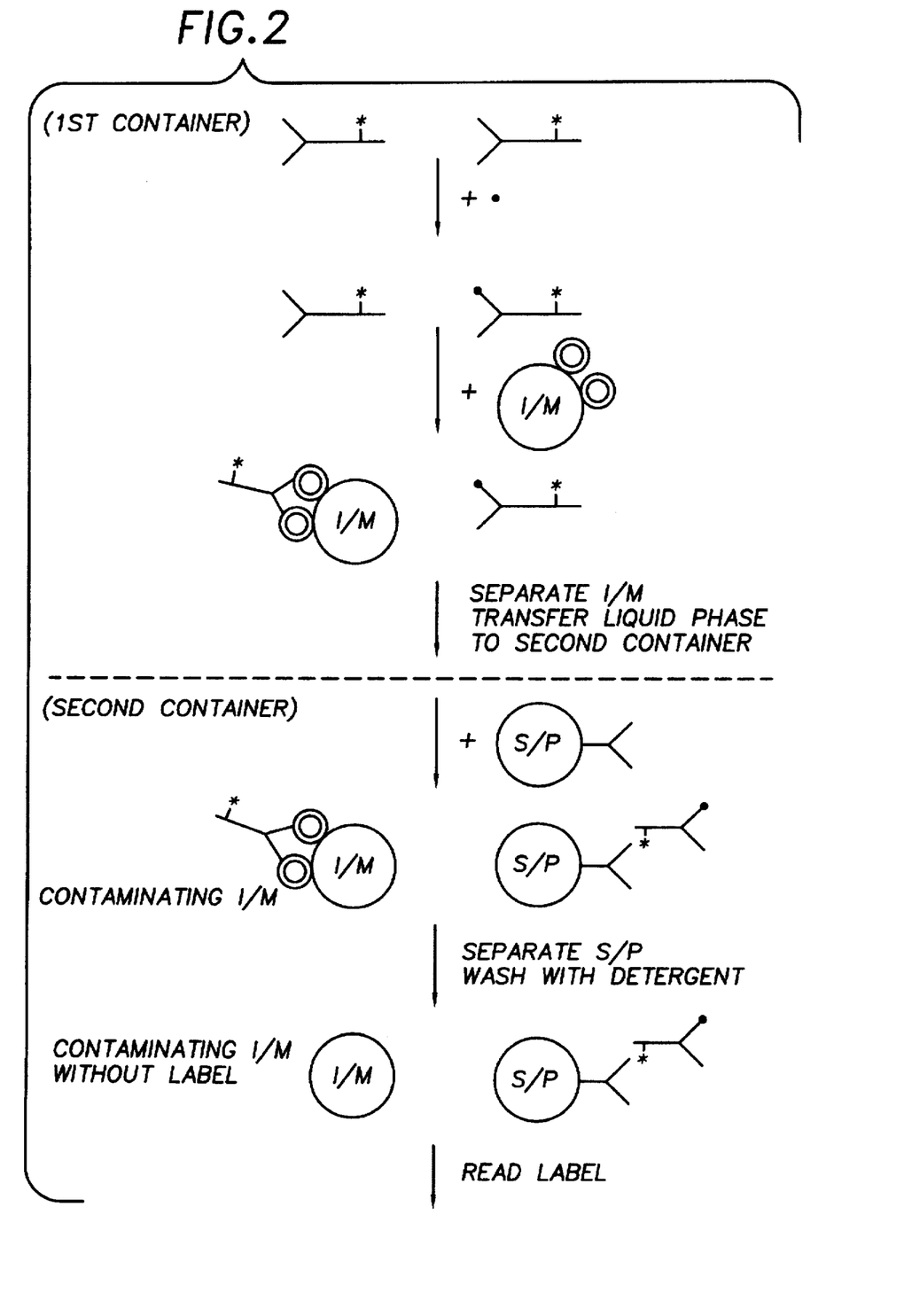
FIG. 2 shows the format of an assay for a monoepitopic analyte when the analyte mimic is attached to the insoluble material via a liposome, and the assay is conducted in two containers.

Another aspect of the present invention is the improvement of the type B noncompetitive assays that utilize more than one cuvette (See FIG. 2) or assays that utilize dipstick, chromatography, electrophoresis, or any other separation method, which in some cases may involve the use of a porous material to separate the insoluble material from the solid phase, the improvement being the use of a reversible bridge for attaching the analyte mimic to the insoluble material.

Figure 4:
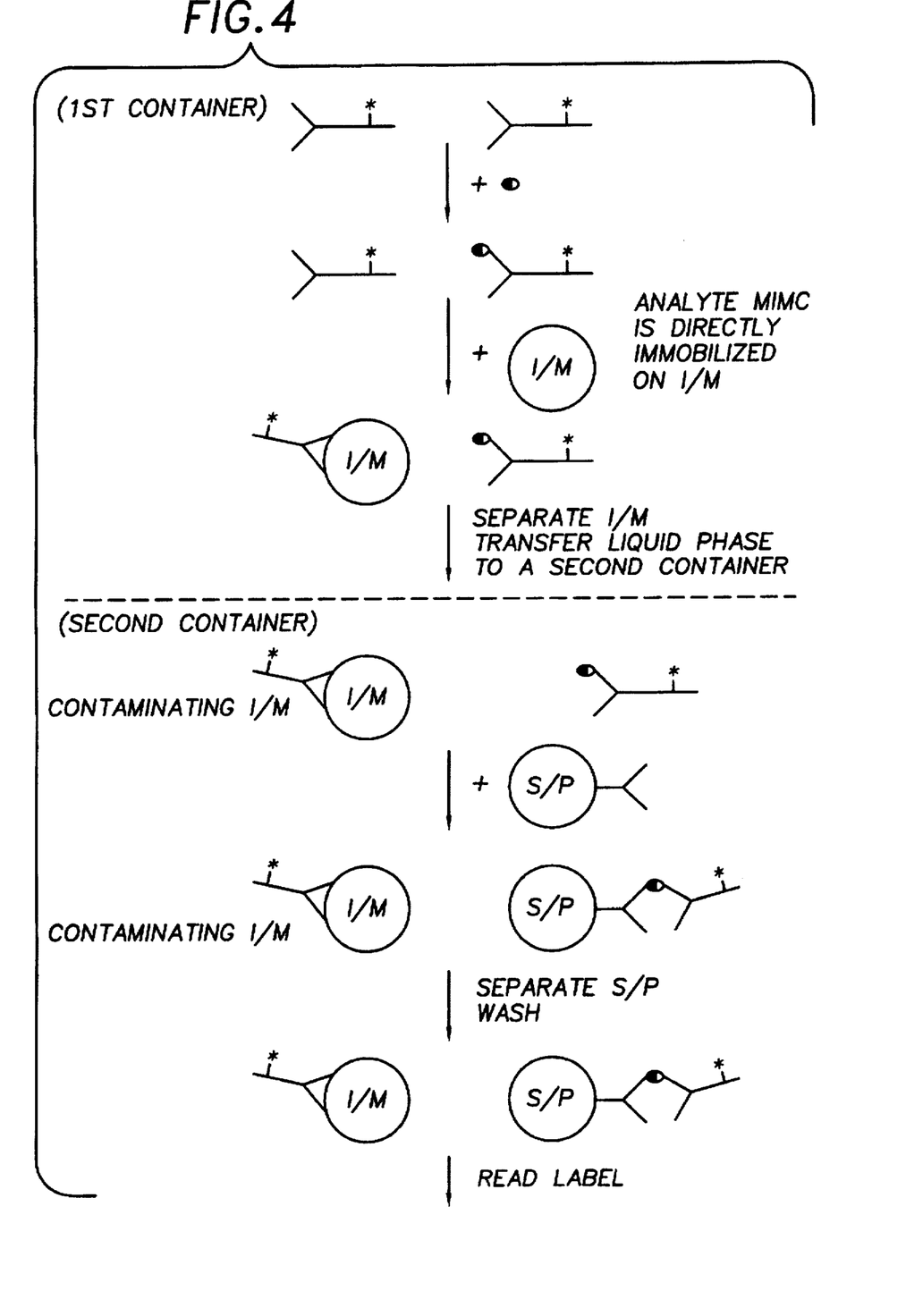
FIG. 4 shows a format for an analyte with more than one epitope, conducted in two containers.
Figure 5:
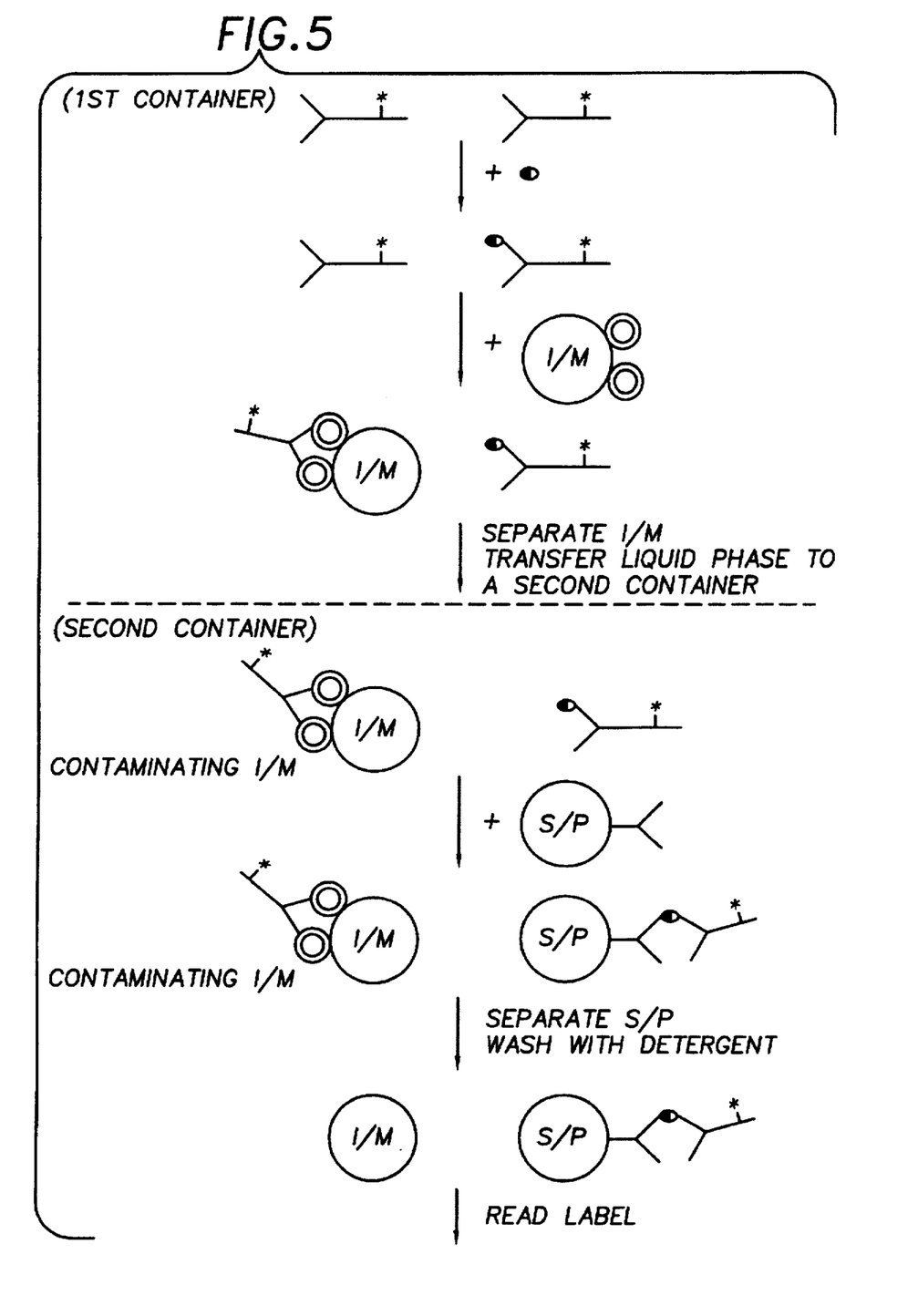
FIG. 5 shows an assay format for an analyte with more than one epitope when the analyte mimic is attached to the insoluble material via a liposome, conducted in two containers. The specific assay format shown in FIG. 6 is for an analyte that is a nucleic acid which has more than one epitope, namely, two or more hybridizable sequences, conducted in two containers.
Figure 7A:
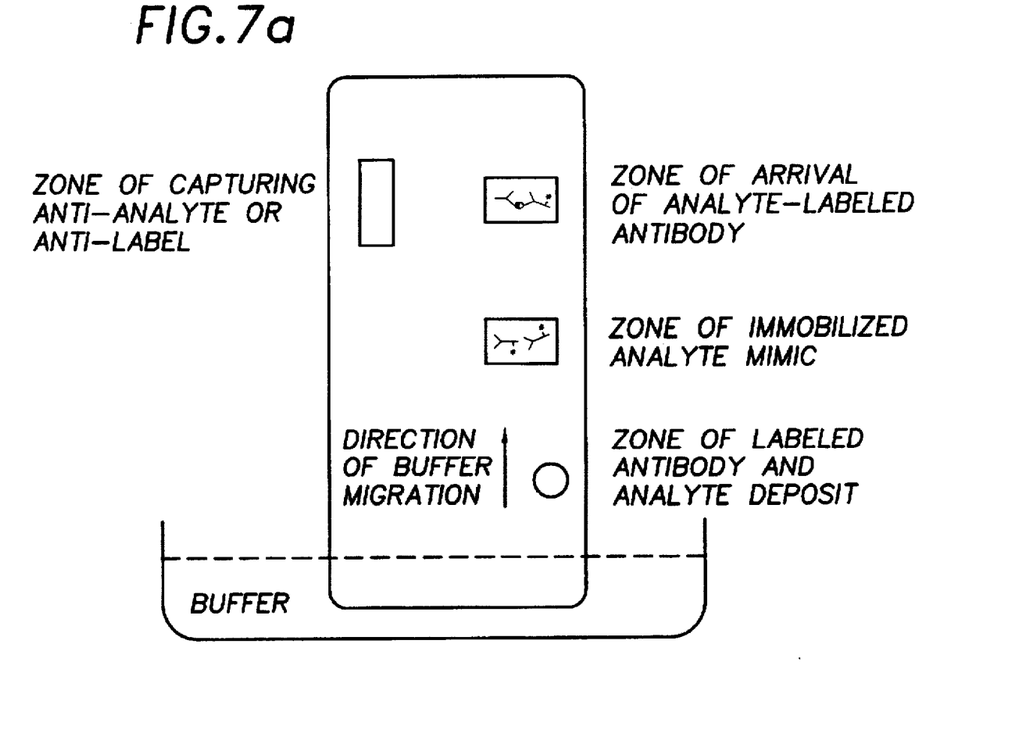
Figure 7B:
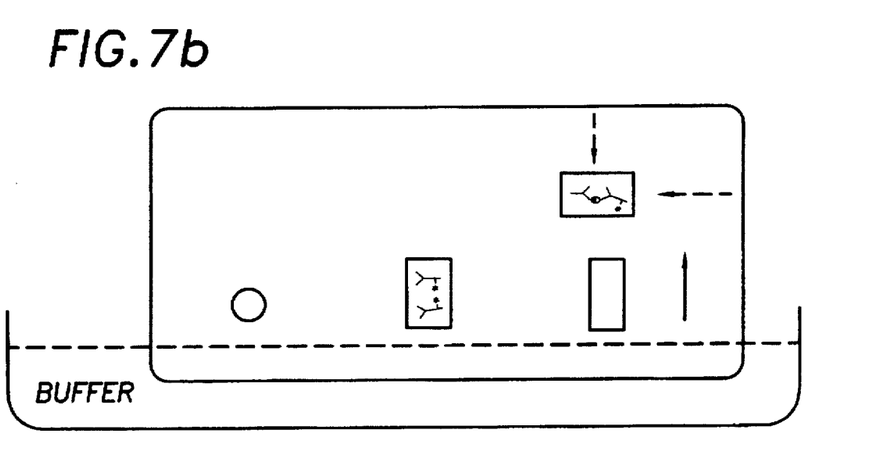

Another aspect of the present invention is an improvement of sensitivity of type A noncompetitive assays via reduction of the NSB of the labeled specific binder to the solid phase and the reaction vessel. The improvement is achieved when the insoluble material is used to remove unreacted labeled specific binder and prevents contact of the solid phase with the unreacted labeled specific binder. The decrease of NSB is achieved because in the presence of very small mount of analyte, most of the labeled specific binder is unreacted (this is true if analyte is incubated with the labeled specific binder for a short time or allowed to substantially reach equilibrium), and, in the absence of analyte, all of the labeled specific binder is unreacted. Thus, removing the unreacted labeled specific binder from the reaction cuvette before adding the solid phase prevents the contact of the solid phase with the majority of the labeled specific binder, thereby leading to substantially less NSB. This aspect is applied to assay formats with one (See FIG. 3) or more (See FIG. 4) containers, and other formats, such as dipstick, chromatography, sensor, pseudohomogenous assay, and others. This aspect of the instant invention may be used with a reversible bridge in connecting the insoluble material with the analyte mimic (see FIG. 5), or without using a reversible bridge (see FIG. 4). A preferred means of separation involves the use of a porous material, such as chromatographic paper, nitrocellulose paper, cellulose acetate, polyacrylamide gel, agarose gel and other porous media. The flow of buffer in porous materials can be effected by capillary forces (see FIG. 7), gravitation, centrifugation, or electrical current.

Multiple variations of these assay procedures are possible. Namely, the assay may be conducted in 1 container or more than 1 container; there may be used in some assays a reversible bridge for binding the insoluble material to the analyte mimic; the reaction can be conducted in a variety of matrices, such as in a true solution, a dipstick, chromatography media, membranes, paper and other porous materials porous material, such as chromatographic paper, nitrocellulose paper, electrophoretic gel and similar media. Porous material is defined herein as a material in which there is a continuous water phase associated with porous solid material, such that some binders may be restricted or immobilized to zones via the porous material, and the transport of liquid phase molecules (or complexes) from one zone to another occurs through the continuous liquid phase. The transport of solutes occur via electrophoretic migration or diffusion, or the liquid phase moves by capillary force or by gravitational force or external pressure. Also, the procedure is applicable to all types of binding assays, including, for example, gene probe assays and receptor assays. The methods described in the present invention can also be combined with other methods. For example, the "immune complex transfer" techniques of Ishikawa et al., 185 Clinica Chimica Acta (1989) 223 and Piran et al. U.S. Pat. No. 5,312,730 (1994) can be used prior to, or after applying, the instant invention, since the combination should provide lower NSB than achievable with each approach separately.

The sample suspected of containing analyte is incubated with Reagent 1, which comprises a labeled specific binder that binds at least a portion of the analyte. After allowing for an incubation period for the analyte and labeled specific binder to react with each other, two additional reagents are then added, either simultaneously (reagents 2 and 3 are pre-mixed) or sequentially (reagent 2 is added first and reagent 3 is added later). Alternatively, after the analyte reacts with the labeled specific binder reagent 2 is added as a dipstick. Alternatively, the analyte-labeled specific binder mixture or the complex formed migrate in a chromatographic or electrophoretic device to a zone containing immobilized reagent 3. In another embodiment the complex is formed in a porous material and then migrates via capillary force through the porous material to a zone containing reagent 3.

Many types of labels have been used in binding assays, for example radiochemical, luminescent, fluorescent, chemiluminescent, enzymatic, liposomal and various metal and non-metal particles. Preferably, the label is a chemiluminescent label (e.g., an acridinium ester) or an enzymatic label. The label can be attached directly to the specific binder by a covalent bond. Alternatively it can be attached indirectly using a binding pair such as biotin/avidin, DNP/anti-DNP or any other binding pair. All are similarly suitable for use in the assays described herein. A recent overview of labels is Howanitz, J. H. in "Immunochemical Assays and Biosensor Technology for the 1990s" Nakamura R. M., Kasahara, Y., and Rechnitz, G. A. Eds., American Association for Microbiology, Washington DC, 1992, p.23–35. On p. 37–53 of this book, Kricka L. describe and compare these and other labels, and in addition some assay formats involving porous materials, which the author calls extralaboratory formats.

Reagent 2 contains a component comprising an analyte or analyte derivative or analyte mimic attached to an insoluble material that allows the reduction of the binding of the previously unreacted labeled specific binder to reagent 3. If it did not reduce this binding, the binder attached to reagent 3 might bind not only to the labeled binder-analyte complex, as desired, but also to the labeled binder which is now bound to the insoluble material, thereby the increasing non-specific signal. In some cases reagent 2 retards binding due to its steric hindrance, and reagent 2 can come in contact with reagent 3. Examples of this insoluble material include particles made of controlled-pore glass, polymer particles, latex, colloidal metal or metal oxide particles, immiscible liquid phase, extended surface, porous paper, porous gel, liposome, emulsion, a system of very small particles that do not settle readily by standing or centrifugation, paramagnetic particles, cellulose beads, cross-linked dextran or any other particle. Extended surface is meant to include relatively flat surfaces, such as the surface of a cuvette or a microtiter plate, and the surface of a relatively large bead, such as one with diameter of greater than 1 mm. Preferred insoluble materials are controlled pore glass, polymer particles, latex particles, cross-linked dextran and extended surfaces. Particle size can vary from 10 nm to several microns in diameter, and smaller materials may include large molecular polymers such as dextran or protein aggregates. Larger beads of any size, flat surfaces, testube wall, dipstick surface, fibers, membranes, rods and discs, or any extended or porous material or particulate surface capable of carrying an immobilized binder. Chromatography techniques are other examples of procedures wherein insoluble materials can be used. Other mechanisms aside from steric hindrance (for example, porosity) also tend to retard the binding to reagent 3. In other cases there is no contact between reagents 2 and 3; instead, extra separation step(s) and more than one container are needed. In other cases reagent 2 and 3 are immobilized onto different zones of the porous medium and the sample and other liquid components of the assay come in contact first with reagent 2 and than with reagent 3.

Although reagent 2 can be in the form of particles, extended surface or porous material, in some embodiments it does not function as usual solid phases function in binding assays, because in these embodiments there is no need to separate reagent 2 from the liquid phase containing the sample and other components of the assay. However, reagent 2 should not excessively adhere to the solid phase or be co-separated with it. Therefore, if the solid phase is separated from the liquid phase containing the sample plus other assay components prior to signal measurement, reagent 2 should remain substantially with the liquid phase and be removed together with it. For these reasons and to distinguish it from a true solid phase, the material used in reagent 2 is referred to as insoluble material.

The component attached to the insoluble material in reagent 2 can be an analyte or a derivative of the analyte. Thus the affinity of the labeled specific binder to this component is, in some cases comparable to the affinity toward the analyte itself. Alternatively, the component may be an analog of the analyte, the affinity of which to the labeled specific binder being much lower by more than one order of magnitude), in this case the binding of the labeled specific binder to reagent 2 is facilitated by avidity (cooperativity between two or more binding site of the binder). (See Piran U. et al. Clinical Chemistry Vol. 39, pp. 879–883, 1993). The component may be a synthetic molecule (such as an organic molecule, a synthetic peptide or an oligonucleotide) or a biologically derived molecule (such as a protein, a peptide, an antibody, an antiidiotypic antibody, receptor, antigen, nucleic acid etc.). In some cases the analyte derivative is attached to the insoluble material via a reversible bridge. Examples of a reversible bridge include immunochemical bond, nucleic acid hybrid, liposomes or some other lipophilic material, as further described hereafter.

Reagent 3 is a solid phase containing an immobilized binder that binds the labeled specific binder-analyte complex. This immobilized binder can be an antibody against (1) the specific binder, (2) the label, or (3) the complex. Alternatively, the immobilized binder can be, in the case when hi- or multi- valent labeled specific binder is used, an analyte or analyte mimic. Furthermore, when the analyte is bi- or multi-valent, the immobilized binder can be an anti-analyte, a specific receptor, or a complementary nucleic acid sequence. In other words, it can bind with any portion of the labeled specific binder-analyte complex. After addition of reagents 2 and 3, the incubation continues in order to bind the labeled specific binder-analyte complex to reagent 3. Finally, the signal emanating from the label associated with the solid phase (reagent 3) is measured. Prior to this signal measurement, the solid phase may be separated and washed, but in the cases of sensors or pseudo-homogeneous assays, separation is not necessary.

Solid phase materials may include: paramagnetic particles (including those made as a composite of magnetic material and polymer, such as magnetic latex, or combined with other materials), particles made of controlled-pore glass, polymer particles, latex, colloidal metal or metal oxide particles, immiscible liquid phase, extended surface, porous paper, porous gel, cellulose beads, cross-linked dextran or any other particle. Particle size can vary from 10 nm to several microns in diameter, larger beads of any size, flat surfaces, testube wall, dipstick surface, fibers, membranes, porous media, rods and discs, or any extended or particulate surface capable of carrying an immobilized binder. Preferably, the solid phase material is either a paramagnetic particle or an extended surface.

Various techniques can be used for separation of the solid phase from the liquid phase, including centrifugation, filtration, settling by gravity, magnetic attraction, electrophoresis, various column chromatographies, capillary forces, etc. The present invention is also compatible with the sensor format, which does not requires removal of the liquid phase, since the sensor can read the signal that is situated near the sensor surface, with only small amount of liquid phase signal being read by the sensor. Also compatible are both batch systems such as those used in automated laboratory instruments, and continuous flow systems. Assay formats involved in "near patient testing", such as dipsticks, immunochromatography and immunoconcentration devices are compatible with the present invention. The same separation techniques may be used to separate the insoluble material from the solid phase, or separated the insoluble material from the liquid phase that contains the analyte-labeled specific binder complex, which is then contacted with reagent 3. If controlled pore glass is used as both the insoluble material and the solid phase, the particles could be separated if they differ by a property that permits separation (e.g., if different particle sizes, they can be separated by filtration or settling rate differences or differential centrifugation). Analogous separation techniques can be used when other insoluble materials and solid phases of the same composition are used.

This novel procedures can be utilized with analytes having one epitope as well as analytes with two or more epitopes, and examples demonstrating variations in the scheme are shown below. In addition, this analytical technique can be used for procedures aside from immunoassays, such as gene probe and receptor assays. As indicated above, the technique is novel for procedures using one or more than one container.

Figure 6:
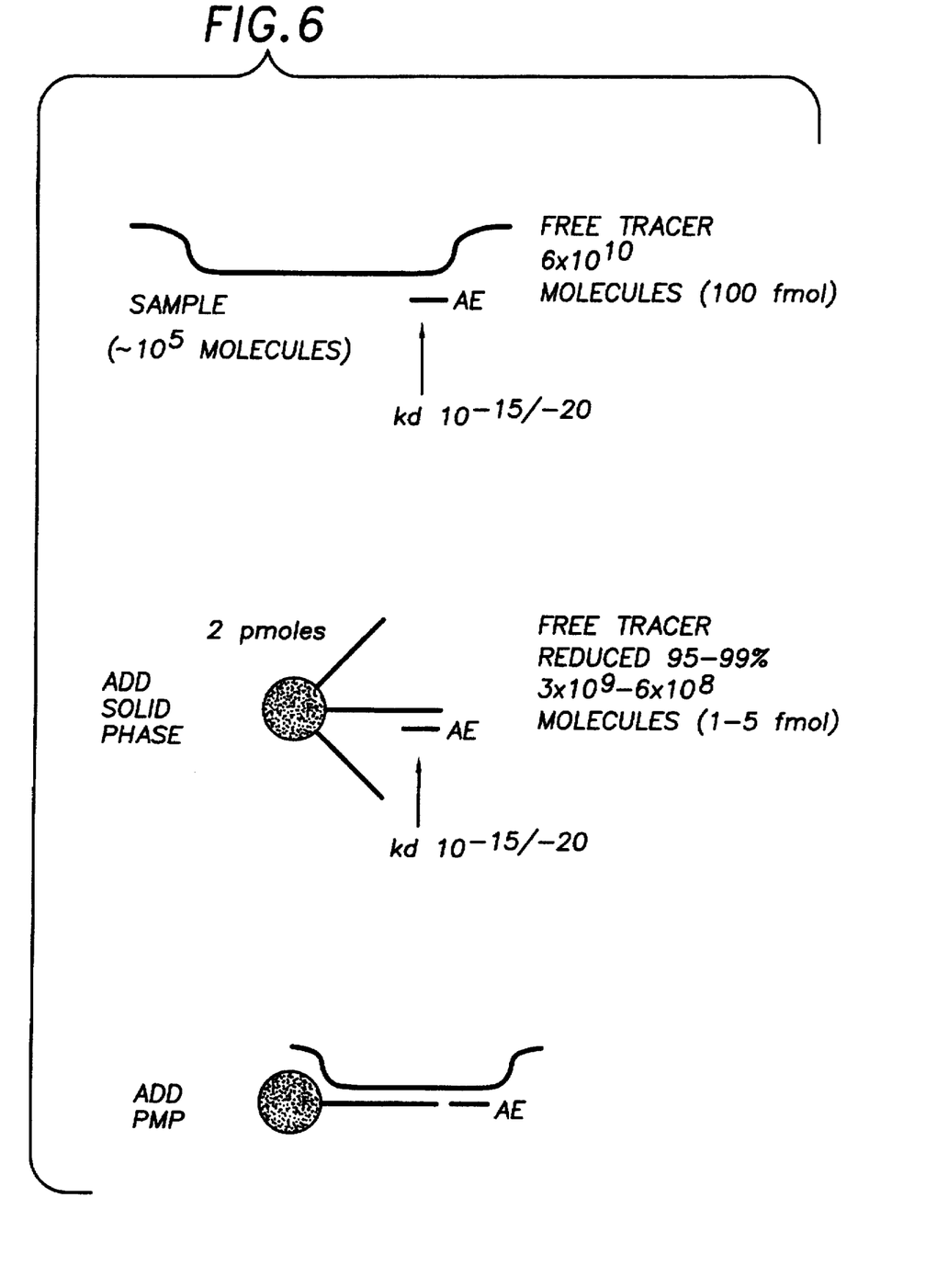

FIG. 6 illustrates a similar reaction mechanism with a gene probe assay. (The gene probe assay depicted does not exhibit a reversible bridge linkage between the probe portion and the solid phase, exemplifying the application of the disclosed technology to situations aside from those incorporating reversible bridges. As a consequence of not using a reversible bridge, no solution is necessary for disrupting the reversible bridge. Furthermore, a probe in this assay incorporates an acridinium ester (AE) label.) Because nucleic acids are polymers of high molecular weight, the solid phase binder can usually be a sequence complementary to the DNA (or RNA) target analyte, (which will be referred to as an epitope), as shown in FIG. 6. However, as in the case of immunoassays for multi-epitopic analytes, in some cases it may be advantageous to use an anti-label (i.e., an antibody against a label), such as an anti-acridinium ester, anti-alkaline phosphatase, anti-horseradish peroxidase, anti-lanthanide or antibody against another label. Alternatively, a ligand may be coupled to the anti-analyte (DNP, biotin, fluorescein etc.), and an anti-ligand may be used as a surrogate to anti-label.

Sample interferences in the instant invention can be reduced by using a smaller sample volume and eliminated by avoiding the use of a binder to a second epitope. (I.e., increased interference is encountered when the sample contains (1) an excess of analyte, which may cause a "hook effect", or (2) a molecule that cross reacts with the binder to the second epitope.) In addition, applicant has surprisingly found that materials that are similar to the analyte in their chemical structure (e.g., cross-reactants) exert a smaller effect on the signal of the novel assay method than on the conventional competitive method: (See Example 1.)

This procedure is compatible with currently existing automated immunoassay instruments and, thus, can be utilized on them without the need to redesign the instruments. The procedure is also convenient for using manually or on non-automated instruments.

The following examples illustrate the procedure of this invention but are not intended to limit its usefulness.

EXAMPLES

Example 1

Preparation of reagents for triiodothyronine (T3) assay with a reversible bridge Monoclonal anti-T3 and anti-DMAE antibodies were produced in mice (A/J) by immunizations and subsequent fusions of the splenocytes with Sp2/O-Ag 14 myeloma cells by the procedure described by Kohler and Milstein in Nature (London) Vol. 256, pp. 494–497 (1975). The immunogen for producing anti-T3 was bovine-serum albumin (BSA-T3), prepared as described by Burke and Shakespeare in J. Endocrinol. Vol. 65, p. 133 (1975). The immunogen for producing anti-DMAE is Keyhole Limphet Haemocyanin KLH-DMAE was prepared with an input ratio of 500:1 DMAE per protein as described by Law et al. in J. Biolumin. Chemilumin. Vol. 4, pp. 88–98 (1989). Mice were immunized 3 times with about 0.1 mg immunogen. The first injection was in complete Freund's adjuvant and subsequent ones in incomplete Freund's adjuvant. Four days prior to the fusion, mice were immunized with 0.01 mg of antigen intravenously. Spleen cells from immunized mice were fused with myeloma cells at a ratio of 5:1. Cell culture supernatants were screened for antibody activity production 7–21 days post fusion, when macroscopic colonies were observed. The tracers used for screening for anti-T3 and anti-DMAE antibodies were 1-125-T3 and DMAE, respectively, and the solid phase was PMP-goat-anti-mouse-IgG. Hybridoma cells secreting the desired antibodies were injected intraperitoneally into pristane-primed mice (CAF). Ascitic fluids from these mice were collected after 3–5 weeks. The antibodies were purified from the ascitic fluid by Protein A column chromatography using Affi-gel Protein A MAPS H kit (Bio-Rad Laboratories, Richmond Calif. 94901) according to the protocol provided with the kit.

Bovine gamma globulin (BGG) was coupled to N-hydroxysuccinimide activated N-hemisuccinate methyl ester of L-3,5-diiodothyronine (T2) as described for L-thyroxine by Law et al in J. Biolumin. chemilumin. Vol. 4, pp. 88–98 (1989). BGG-T2 was coupled to CNBr-activated Sepharose 6B (Pharmacia, Piscataway, N.J.) and used for affinity purification of anti-T3 according to the manufacturer's instructions. Anti-DNP was prepared and coupled to PMP as described by Piran et al. (1994) U.S. Pat. No. 5,312,730. Paramagnetic particles (PMP) coupled to proteins were prepared as described by Groman et al. BioTechniques, Vol. 3, pp. 156–160 (1985). BGG-T2 was coupled to controlled pore glass (CPG) particles by essentially the same method described therein. The CPG itself (same material used in Ciba Corning's Immophase products; 1 micron diameter; has aminosilane groups on its surface) was prepared essentially as described by H. H. Weetall. (See Science, 166:615, 1969; Nature, 223:959, 1969; Biochim and Biophys Acta 185:464, 1969.) The protein A purified anti-T3 and anti-DMAE and affinity purified anti-T3 were labeled with DMAE as described by Law et al in J. Biolumin. Chemilumin. Vol. 4, pp. 88–98(1989).

Example 2

Assay for T3 with a liposomal reversible bridge

This example illustrates the novel procedure as it applies to a monoepitopic analyte (T3). Because there is only one epitope on the analyte, the binder attached to the second solid phase cannot be an anti-analyte, but a binder of any part of the labeled anti-T3; in this case it is an anti-label. This solid phase is a universal reagent that can be used for assays of a wide variety of analytes.

Liposomes bearing DNP and BGG-T2 are prepared as described by Piran et al. (1994) U.S. Pat. No. 5,312,730, except that BGG-T2 is coupled to the liposomes instead of antibodies. These liposomes are pre-incubated with PMP-anti-DNP and washed once to remove unbound liposomes. The non-competitive assay of T3 is performed on the ACS: 180 instrument (Ciba Corning Diagnostics Corp.). The sample probe delivers 0.01 ml sample or standard and 0.05 ml 0.15N NaOH to the reaction cuvette. Reagent probe 1 delivers 0.1 ml affinity purified, DMAE-labeled anti-T3, $2 \times 10^{-6}$ relative light units (RLU) in Buffer A containing 140 mM sodium phosphate, 20 mM sodium barbital, 4 mM sodium chloride, 1 mM ethylenediamine-tetraacetic acid (EDTA), 0.15 g/L 8-anilino-1-naphtalene-sulfonic acid (ANS), 1 g/L sodium azide, 0.02 g/L bovine gamma globulin (BGG), and 2.5 g/L bovine serum albumin (BSA), pH 6.6. After 2.5 min incubation at 37 C. reagent probe 2 delivered 0.1 ml of CPG-liposome-BGG-T2 in Buffer B containing 50 mM sodium phosphate, 150 mM sodium chloride, 1 mM EDTA, 0.2 g/L sodium azide, and 1 g/L BSA, pH 7.4. After an additional 2.5 min incubation reagent probe 3 delivers 0.05 mg of PMP-anti-DMAE in 0.5 ml Buffer B. Following another 2.5 min incubation the instrument attracts the PMP to the cuvette wall and performs two washes with 1 ml of 0.1% Triton X-100 (v/w) and 1% Pluronic-F108 in deonized water. The instrument then adds 0.3 ml of 5%(v/v) $H_2O_2$ in 0.1N $HNO_3$ and 0.3 ml of 0.1N NaOH, 0.5% (w/V) cationic surfactant Arquad, and the light is collected in the instrument's photomultiplier tube and is expressed as RLU's. (See FIG. 1 for a scheme of the reaction).

Example 3

Preparation of reagents for thyroid stimulating hormone (TSH) assay with use of two containers This example discusses the procedure for an analyte which has at least 2 epitopes (thyroid stimulating hormone or TSH), where the solid phase binder binds directly to a second epitope of the analyte. Monoclonal anti-TSH antibodies (7A10 and 11A8) were prepared by immunizations of mice (Balb/c) with human TSH essentially by the methods described in Example 1. An antiidiotypic anti-anti-TSH (7A10) was produced by immunizing mice with Fab2 fragments of anti-TSH (7A10) coupled to maleimide-activated keyhole limphet heamocyanine (Pierce Chemical Co.). The Fab2 fragments was prepared by digestion with pepsin as described in "Antibodies: a laboratory manual" E. D. Harlow and D. Lane Eds. Cold Spring Harbor Pub. 1988, pp. 630–1. Screening for anti-TSH antibodies was done with I-125-TSH and PMP-goat-anti-mouse-IgG. For screening the antiidiotype producing cells, PMP-anti-TSH (7A 10) and DMAE-anti-TSH (7A10) were incubated with cell culture supernatants and the presence of antiidiotype was detected by formation of a bridge between the PMP and the label. Inhibition of the bridge formation by TSH was used to confirm the specificity of the antiidiotype. Anti-TSH (7A10) was labeled with DMAE, and anti-TSH (11A8) and antiidiotype anti-anti-TSH (7A 10) was immobilized on PMP and CPG, respectively as described in Example 1.

Example 4

TSH assay with use of one container

Figure 3:
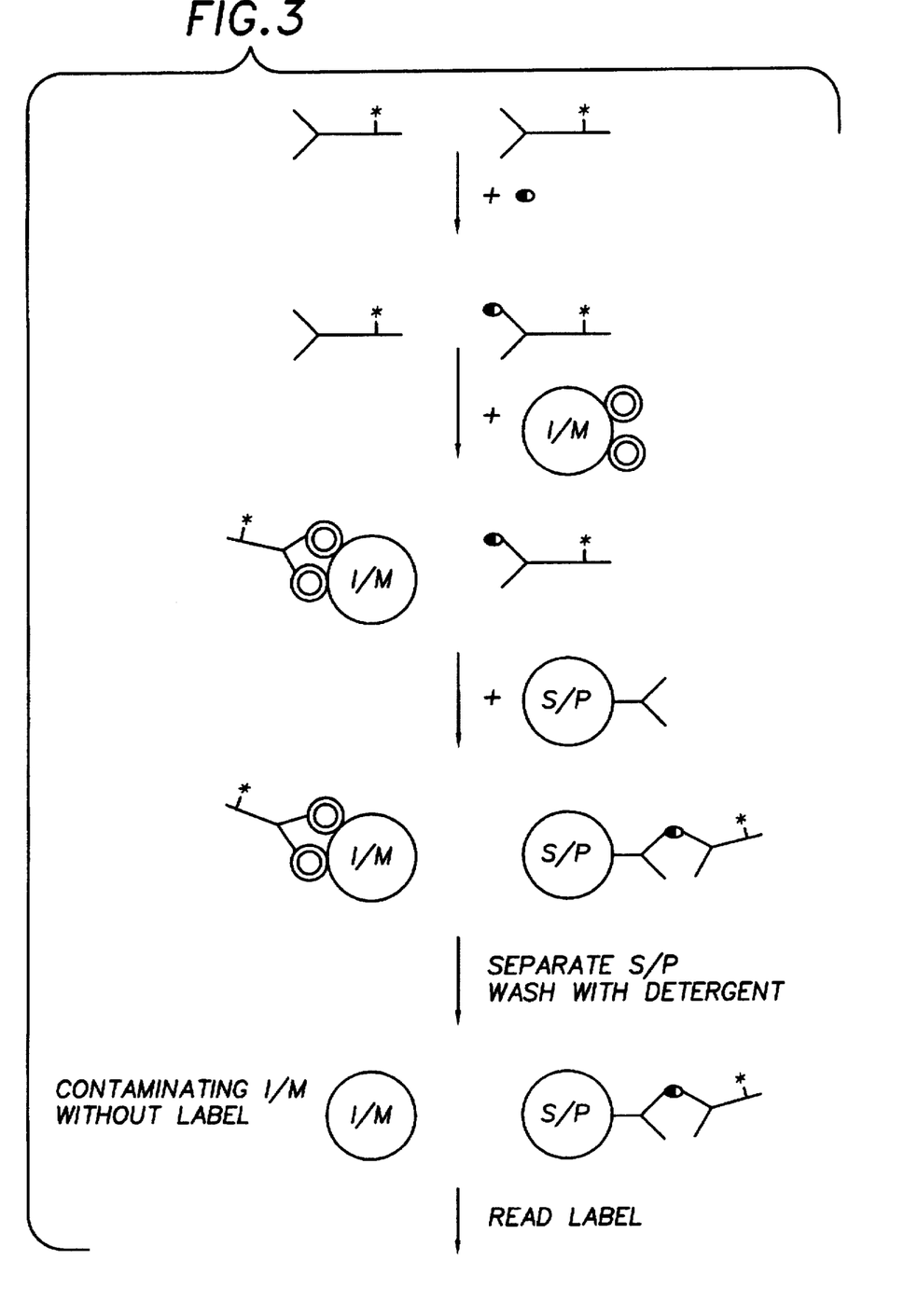
FIG. 3 depicts the assay format for an analyte containing more than one epitope, when the analyte mimic is attached to the insoluble material via a liposome, conducted in one container.

The TSH assay is performed on the ACS: 180 instrument. The sample probe adds 0.1 ml standard to the reaction cuvette. Reagent probe 1 adds 0.1 ml DMAE-anti-TSH (7A10) 2×10e7 RLU's in Buffer B. After 2.5 min incubation at 37 C. reagent probe 2 adds 0.1 ml 0.2 mg CPG-antiidiotype (anti-11A10) in Buffer B. After 2.5 min incubation at 37 C. reagent probe 3 adds 0.25 ml of 0.05 mg PMP-anti-DMAE or PMP-anti-TSH (11A8) in Buffer B. Following 2.5 min incubation at 37 C., magnetic separations and two washes with deionized water, the chemiluminescence associated with the PMP's is measured by the instrument. The mechanism of the assay is depicted in FIG. 3.

Example 5

Nucleic Acid Assays with Background Reduction Step

In the standard assay for the ΔF-508 cystic fibrosis mutation sequence varying amounts of a synthetic DNA target sequence (ΔF-508, SEQ ID NO 1) were hybridized with two DNA probes at 45° C. in hybridization buffer (600 mM NaCl, 60 mM sodium citrate, 10 mM Tris, pH 7.51 mM EDTA, 5% dextran sulfate, 0.1% BSA, and 0.02% Tween-20). One of the DNA probes, 508 CF (SEQ ID NO 2), was labeled at its 3'terminus with an acridinium ester essentially as described in Example 1 for labeling antibodies. Purification of the labeled probe was accomplished by C18 Reversed Phase High Performance Liquid Chromatography. The second DNA probe, PMP.508 (SEQ ID NO 3), was immobilized on paramagnetic particles via glutaraldehyde as described in Example 1 for immobilizing antibodies, and 10 ug PMP.508 was added to the incubation mixture followed by incubation at 45° C. for 1 hr. The particles were separated magnetically, the supernatant aspirated and the particles washed with wash buffer (300 mM NaCl, 30 mM sodium citrate, 0.1% Tween-20). The magnetic particles were resuspended in ligation buffer (50 mM Tris, pH 7.6, 10 mM $MgCl_2$, 1 mM DTT, 1 mM ATP, 200 mM NaCl, and 5% polyethylene glycol) containing 2 units T4 DNA ligase. The ligation reaction was carried out at 37° C. for 15 minutes. The particles were separated and washed as described above. Hybridized but unligated 508.CF-AE was removed by resuspending the particles in $H_2O$, and incubating at 650° C. for 5 minutes. The magnetic particles were separated and washed then resuspended in a solution (50 mM Tris, pH 7.5, 10 mM $MgCl_2$) containing DNase I (0.005 mg in 0.1 ml buffer) and the chemiluminescence determined in a luminometer.

In the assay employing a background signal reduction step, the synthetic targets were incubated in hybridization buffer with 508.CF-AE at 45° C. for 15 minutes. The unhybridized 508.CF-AE was captured by specific hybridization with a probe, LCF4-CPG (SEQ ID NO 4), a portion of whose sequence was complementary to 508.CF-AE. This probe had been immobilized onto controlled pore glass (CPG) by first immobilizing bovine gamma globulin (to reduce nonspecific adsorption) via glutaraldehyde and then immobilizing to it the LCF4 probe which had been activated with bis(sulfosuccinimydyl)suberate. The LCF4-CPG was separated by centrifugation and one-half to three-fourths of the supernatant volume transferred to a tube containing 10 ug PMP.508 in hybridization buffer. The remainder of the assay was carried out as described above. A similar background reduction-hybridization-ligation assay was carried with a version of the 508.CF probe (508.CF-2AE, SEQ ID NO 5) which had been labeled with two acridinium esters rather than one.

Figure 8:
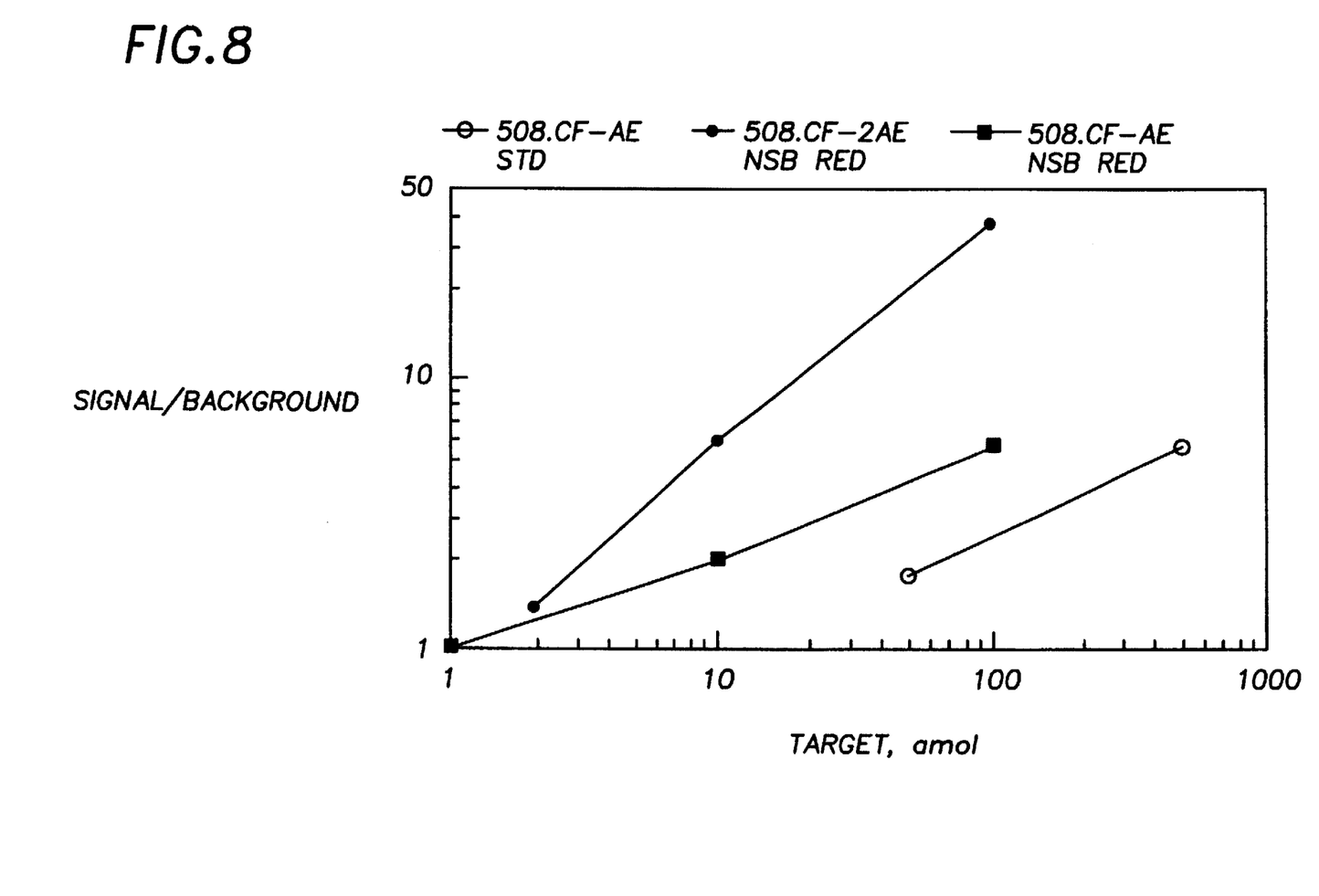
FIG. 8 shows results obtained in a gene probe assay for a Cystic Fibrosis mutation.

The results of these assays are summarized in FIG. 8. The background reduction step improved the sensitivity of the standard assay. The background signal (signal from the assay containing no added target) was reduced to close to that of the instrument background. For the background reduction assay with 508.CF-AE, the detectability of the label now becomes limiting to assay sensitivity. The sensitivity was further improved by the use of 508.CF-2AE in the background reduction assay to provide a larger specific signal.

---

What is claimed is:

1. A binding assay procedure for determination of an analyte, such procedure being conducted in one container, by
    a. mixing the solution containing the analyte with a labeled specific binder which binds to a first binding site on the analyte to form an analyte-labeled specific binder complex,
    b. contacting the solution from step a with one or more materials which comprise
        1. a reagent which contains an insoluble material which is attached by a reversible bridge to an analyte derivative or an analyte mimic that binds to the labeled specific binder that had not bound analyte to form an insoluble material-labeled specific binder complex and
        2. a reagent that contains a second binder which binds to one portion of the analyte-labeled specific binder complex, such second binder being attached to a solid phase,
    such that the insoluble material, by binding to the labeled specific binder that had not bound analyte, inhibits the binding of the unreacted labeled specific binder to the solid phase,
    c. separating the solid phase from the insoluble material and the liquid components of the reaction mixture and washing the solid phase with a solution containing one or more materials that disrupt the reversible bridge between the label and any insoluble material remaining in the container with said solid phase,
    d. measuring the label associated with the solid phase, and
    e. determining the amount of analyte by comparing the amount of said label measured to that in a reference solution.

2. An assay procedure of claim 1 in which the insoluble material is controlled pore glass, the solid phase is controlled pore glass or a paramagnetic particle, and the label is an acridinium ester.

3. A binding assay procedure for determination of an analyte, such procedure being conducted in more than one container, by
    a. mixing the solution containing the analyte with a labeled specific binder which binds to a first binding site on the analyte to form an analyte-labeled specific binder complex in a first container,
    b. contacting the solution from step a with one or more materials which comprise a reagent which contains an insoluble material which is attached via a reversible bridge to an analyte derivative or an analyte mimic that binds the labeled specific binder that had not bound analyte to form an insoluble material-labeled specific binder complex,
    c. separating said insoluble material from solution containing said analyte-labeled specific binder complex,
    d. transferring said solution containing the analyte-labeled specific binder to another container,
    e. mixing it with a reagent that contains a second binder which binds to one portion of the analyte-labeled specific binder complex, such second binder being bound to a solid phase, in order to bind the analyte-labeled specific binder to the solid phase, f. separating said solid phase and washing it with a solution containing one or more materials that disrupt the reversible bridge between the label and any insoluble material remaining in the container with said solid phase, and measuring the label associated with the solid phase, and g. determining the amount of analyte by comparing the amount of said label measured to that in a reference solution.

4. An assay procedure of claim 3 in which the insoluble material is controlled pore glass, the solid phase is controlled pore glass or a paramagnetic particle, and the label is an acridinium ester.

5. An assay procedure of claim 3 wherein (a) the analyte derivative or analyte mimic is attached directly to the insoluble material (b) there is no usage of the solution that disrupts said bridge and (c) the analyte has 2 or more binding sites.

6. A binding assay procedure for determination of an analyte, such procedure being conducted in or on a porous material, comprising a. contacting a solution containing said analyte with a labeled specific binder that binds to a first binding site on the analyte to form an analyte-labeled specific binder complex, said binder being in a first zone of said porous material, b. causing said complex and the unreacted labeled specific binder to migrate to a second zone in said porous material, said second zone containing an analyte derivative or an analyte mimic which is attached via a reversible bridge to said porous material directly or via an immobilized insoluble material, to form a complex containing (1) a labeled specific binder-analyte derivative-reversible bridge-porous material, (2) a labeled specific binder-analyte mimic-reversible bridge-porous material, (3) a labeled specific binder-analyte derivative-reversible bridge-insoluble material-porous material or (4) a labeled specific binder-analyte mimic-reversible bridge-insoluble material-porous material complex, c. causing said analyte-labeled specific binder complex to migrate to a third zone in the porous material, said zone containing an immobilized second binder which binds to one portion of the analyte-labeled specific binder complex, d. washing said third zone with a solution that contains one or more materials that disrupt the reversible bridge between the label and the insoluble or porous material, e. measuring the label associated with said third zone, and f. determining the amount of said analyte by comparing the amount of said label with that in a reference solution.

7. An assay procedure of claim 6 in which the insoluble material is controlled pore glass, the porous material is chromatographic paper, polyacrylamide gel, or agarose gel, and the label is an acridinium ester.

* * * * *